(12) United States Patent
Siess et al.

(10) Patent No.: US 10,801,511 B2
(45) Date of Patent: Oct. 13, 2020

(54) ROTOR FOR A FLUID PUMP AND METHOD AND MOLD FOR THE PRODUCTION THEREOF

(71) Applicant: ECP ENTWICKLUNGSGESELLSCHAFT MBH, Berlin (DE)

(72) Inventors: Thorsten Siess, Aachen (DE); Mario Scheckel, Berlin (DE)

(73) Assignee: ECP ENTWICKLUNGSGESELLSCHAFT MBH, Aachen (DE)

( * ) Notice: Subject to any disclaimer, the term of this patent is extended or adjusted under 35 U.S.C. 154(b) by 296 days.

(21) Appl. No.: 15/570,128

(22) PCT Filed: Apr. 29, 2016

(86) PCT No.: PCT/EP2016/059708
§ 371 (c)(1),
(2) Date: Oct. 27, 2017

(87) PCT Pub. No.: WO2016/174257
PCT Pub. Date: Nov. 3, 2016

(65) Prior Publication Data
US 2018/0149165 A1 May 31, 2018

(30) Foreign Application Priority Data

Apr. 30, 2015 (EP) ..................................... 15166042
Apr. 30, 2015 (EP) ..................................... 15166045

(51) Int. Cl.
*F04D 29/02* (2006.01)
*A61M 1/10* (2006.01)
(Continued)

(52) U.S. Cl.
CPC ......... *F04D 29/026* (2013.01); *A61M 1/1024* (2014.02); *A61M 1/125* (2014.02);
(Continued)

(58) Field of Classification Search
CPC ........ F04D 29/026; F04D 29/181; F04D 3/02; A61M 1/1024; A61M 1/125;
(Continued)

(56) References Cited

U.S. PATENT DOCUMENTS

2013/0177409 A1 7/2013 Schumacher
2014/0301822 A1 10/2014 Scheckel
2018/0149164 A1* 5/2018 Siess .................. A61M 1/1024

FOREIGN PATENT DOCUMENTS

EP 2407185 A1 1/2012
EP 2407187 A1 1/2012
WO 2012/007140 A1 1/2012

OTHER PUBLICATIONS

English Translation of PCT International Search Report for PCT/EP2016/059708, dated Oct. 10, 2016 (3 pages).

* cited by examiner

*Primary Examiner* — Lindsey G Wehrheim
(74) *Attorney, Agent, or Firm* — Botos Churchill IP Law LLP

(57) ABSTRACT

The invention relates to a rotor for a compressible fluid pump, in particular a blood pump that can be introduced through a blood vessel into a patient's body, wherein said rotor comprises one or more conveying elements (15), is compressible and expandable between a first compressed state and a second radially expanded state, is made at least partially from a plastic reinforced with reinforcing elements, in particular fibers (10, 11, 13, 18, 19, 55, 56, 62, 63) and is provided for rotation about an axis of rotation (14). According to the invention, the rotor is tensioned in the first,
(Continued)

compressed state and free from external stresses in the second, expanded state. A third state exists, which the rotor (42) occupies in the operating state under load. The reinforcing elements, in particular fibers, extend in the rotor in the third state at least in sections in a stretched manner.

35 Claims, 10 Drawing Sheets

(51) Int. Cl.
*A61M 1/12* (2006.01)
*B29C 45/16* (2006.01)
*B29C 45/27* (2006.01)
*B29C 45/72* (2006.01)
*F04D 29/18* (2006.01)
*B29L 31/00* (2006.01)
*F04D 3/02* (2006.01)

(52) U.S. Cl.
CPC .......... *B29C 45/16* (2013.01); *B29C 45/2708* (2013.01); *B29C 45/7207* (2013.01); *F04D 29/181* (2013.01); *A61M 1/101* (2013.01); *A61M 1/1012* (2014.02); *A61M 1/1034* (2014.02); *A61M 1/122* (2014.02); *B29L 2031/7498* (2013.01); *F04D 3/02* (2013.01)

(58) Field of Classification Search
CPC .. A61M 1/1012; A61M 1/1034; A61M 1/122; B29C 45/16; B29C 45/2708; B29C 45/7207; B29L 2031/7498
See application file for complete search history.

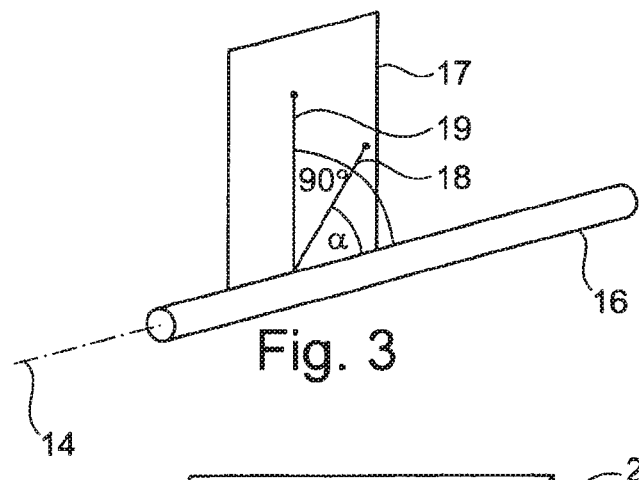
Fig. 3
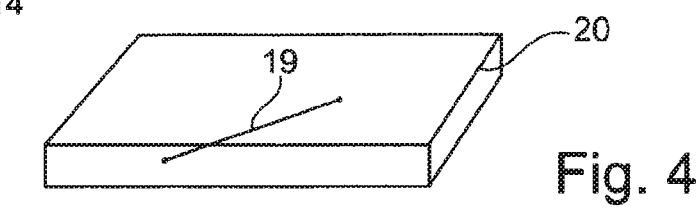
Fig. 4
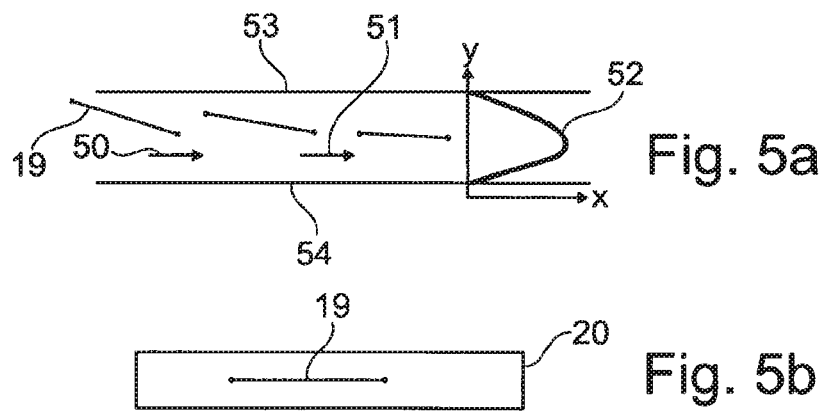
Fig. 5a
Fig. 5b
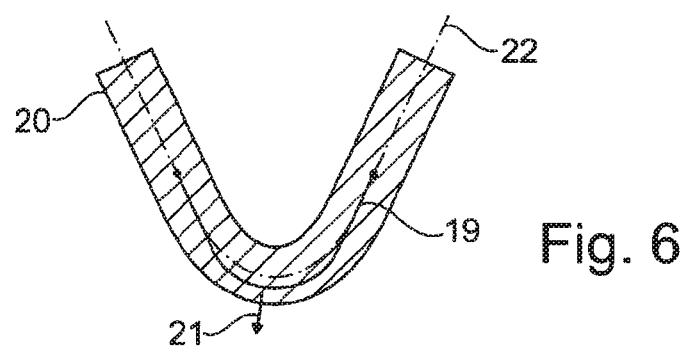
Fig. 6

ROTOR FOR A FLUID PUMP AND METHOD AND MOLD FOR THE PRODUCTION THEREOF

CROSS-REFERENCE TO RELATED APPLICATIONS

This application is a United States National Stage filing under 35 U.S.C. § 371 of International Application No. PCT/EP2016/059708, filed on Apr. 29, 2016, which claims the benefit of European Patent Application Nos. 15166042.0, filed on Apr. 30, 2015 and 15166045.3 filed on Apr. 30, 2015, the contents of all of which are incorporated by reference herein in their entirety. International Application No. PCT/EP2016/059708 was published under PCT Article 21(2) in German.

The present patent application lies in the field of mechanics and relates specifically to rotors for fluid pumps. It can be used particularly advantageously in the field of medical engineering with respect to catheter pumps.

In the field of fluid pumps, rotor pumps are already known in various embodiments in the form of axial pumps or radial pumps. In both cases, the fluid to be conveyed is accelerated, either in the axial direction or in the radial direction, by a rotation of a rotor and impeller elements secured to said rotor.

Pumps of this type can also be compressed already in accordance with the prior art so as to arrange or transport them in a space-saving manner. This applies in particular to catheter pumps for medical application, which often can be radially compressed and expanded so as to be able to be transported to the site of application through a catheter or through cavities in the body of a patient and then expanded at the site of application, before being set in operation. Such pumps are used for example to assist a patient's heart in the pumping of blood, and for this purpose are advanced through a blood vessel as far as, or into a chamber of the heart.

In this case, particular challenges are posed by the small size of the rotor and additionally the compressibility thereof. In the expanded state, in spite of its compressibility, the rotor must reproducibly assume an operating form that changes as little as possible, even in the event of operation at maximum rotational conveying speeds, in order to prevent a reduction in efficiency and also damage to the blood constituents to be conveyed.

For this reason, the use of a wide range of materials and material combinations has already been considered and examined for the aforementioned purpose. By way of example, the use of a wide range of elastomers, also in conjunction with a fiber reinforcement, is already known from WO 2010/063494 A1.

WO 2012/007141 A1 discloses a reinforcement of a pump rotor by fibers, which can be arranged in the rotor in oriented form, for example in the radial direction.

Lastly, WO 2012/007140 A1 discloses a pump rotor with reinforcement elements which can be provided substantially outside the impeller elements, for example on surfaces thereof.

Against the background of the prior art, the object of the present invention thus lies in creating a plastic rotor of the above-mentioned type which has a minimal relaxation after deformations between the compressed and the expanded state as well as the most accurate possible reproducibility of its geometry, at least in the operating state.

The object is achieved by a rotor, a method for producing a rotor, and a corresponding mold for a rotor.

This results, inter alia, in a rotor for a compressible fluid pump, in particular a blood pump which can be introduced through a blood vessel into a patient's body, which rotor has one or more impeller elements and can be radially compressed and expanded between a first, compressed state and a second, radially expanded state, and consists at least in part of a plastic reinforced by strand-like reinforcement elements, in particular fibers, and is intended to rotate about an axis of rotation, wherein the rotor is tensioned in the first, compressed state and is free from external stresses in the second, expanded state, and wherein a third state exists, which the rotor assumes in the operating state under load, characterized in that the fibers in the rotor in the third state run in a stretched manner, at least sectionally.

Fluid pumps of this type are usually introduced in the compressed state into a blood vessel, for example an artery, through a port and are advanced until in the vicinity of the heart or partially within a patient's heart so as to be expanded there. The invention, however, is not limited to blood pumps of this type, and instead also comprises other types of blood pumps having compressible and expandable rotors or other fluid pumps which can be introduced into systems of cavities for medical or non-medical purposes. In the compressed state, the rotor of such a pump is usually under a radial compressive stress, for example by being constricted by an outer sleeve. By way of example, the outer sleeve can be a catheter, from which the pump is slid out for expansion. However, the rotor of the pump can also be constricted in the compressed state by any other type of outer sleeve.

If the compressing force is eliminated, the pump relaxes, or at least the rotor of the pump relaxes, and transitions into a second, expanded relaxed state, in which the radial extent of the rotor increases significantly compared to the first, compressed state.

If the pump is then set in operation by driving the rotor in rotation, and a fluid is conveyed, the rotor transitions into an operating state, which corresponds to a loaded state under the load of the conveyed liquid. Particularly this operating state should take place with a defined geometric design of the rotor, which should be independent of the magnitude of the load to the greatest possible extent. In addition, the rotor should pass through a minimal change of form as it transitions between the second and the third state. However, in the third state under the load of the conveyed liquid, the rotor can be deformed in such a way that the diameter of the rotor enlarges compared to the second, expanded state.

The strand-like reinforcement elements/fibers which reinforce the plastic material of the rotor should be arranged in the matrix of the plastic material in such a way that in the third state they run in a stretched manner at least sectionally and thus stabilize the form of the rotor with respect to the load. Here, the fibers are intended to be subjected to a tensile load in the longitudinal direction. Since the fibers are practically non-stretchable in the longitudinal direction, corresponding loads in the longitudinal direction of the fibers result in practically no significant change of form of the matrix. The rotor or individual elements of the rotor, for example the impeller elements, can thus change in form from compressed state to operating state without difficulty until the fibers are stretched at least in part. At this point, due to the anchoring of the fibers in the plastic material of the rotor, a movement in the longitudinal direction of the fibers is made practically impossible, even under load, at least in the region in which the fibers are stretched.

A particular embodiment of the solution by way of example provides that the reinforcement elements/fibers in the third state (operating state) of the rotor run stretched at least sectionally in regions of the rotor in which said rotor experiences an elongation stress, and run substantially in the direction of the elongation stress.

The reinforcement elements/fibers should be arranged at least in part in the direction in which elongation stresses occur in the rotor so that these elongation stresses are intercepted by take-up of the longitudinal forces into the fibers and the form of the rotor remains practically unchanged or does not change further.

By way of example, this requires at least some of the reinforcement elements/fibers to run in the impeller elements of the rotor outside what are known as the neutral fibers. In the region of what are known as the neutral fibers and/or neutral plane in the field of bending mechanics, a high-tensile fiber would not provide any additional stabilization of the rotor. The neutral fiber in bending technology, in the rotors described here, is generally a plane, and therefore the term bending neutral plane or neutral plane will be used hereinafter for improved clarity of the term.

It can therefore be provided that more than half of the reinforcement elements/fibers are arranged in regions of the rotor and/or the impeller elements in which this/these experiences/experience elongation stresses in the operating state. Here, it is particularly advantageous if many fibers are arranged in the region of the rotor or of an impeller element that experiences elongation stresses under load.

In addition, it can be provided that, in the case of the rotor, there are substantially no differences between the second, expanded state and the third, operating state in respect of the outer form.

For particularly good stabilization of the rotor on the whole, it can also be provided by way of example that reinforcement elements/fibers are provided which extend in the radial direction beyond the axis of rotation. Individual impeller elements are thus stabilized not only against bending, but also with respect to a pivoting motion about a part of the rotor near the axis of rotation, for example a hub.

In addition, it can be provided advantageously that in the operating state at least some of the fibers, in particular the majority of the reinforcement elements/fibers, sectionally run in a straight line. Other straight portions or also curved portions of the fibers can be provided between the portions in which the reinforcement elements/fibers run in a straight line.

It can also be provided that in the operating state at least some of the fibers, in particular the majority of the reinforcement elements/fibers, run along the longitudinal direction of the impeller elements with a smaller curvature than the neutral plane of the impellers in the sense of the science of strength of materials. As a result of this arrangement of the reinforcement elements/fibers, it is ensured that the reinforcement fibers on the one hand are already heavily stretched in the operating state and that they on the other hand run outside the neutral plane of the impeller elements and therefore in regions that can experience elongation stresses under load.

In addition, it can also be provided that the plastic of the rotor has a Shore hardness <100 D, in particular <80 D. Due to the low Shore hardness, which for example can also be selected to be less than 80 D, it is made possible, with heavy bending or buckling of the material, for the embedded reinforcement elements/fibers to push into the resilient base material and thus limit the radius of curvature downwardly. This results in a reduction of the risk of breakage of the elements/fibers.

In addition, in the case of a rotor of this type, it can also be provided that a first proportion of more than 30%, in particular more than 50%, of the reinforcement elements/fibers in the expanded state of the rotor runs in a substantially stretched manner from a portion disposed closest to the rotor axis to a second portion disposed further away from the axis of rotation. As a result of this positioning, orientation and forming of the reinforcement elements/fibers, an overstretching of the rotor beyond the expanded state is effectively avoided.

The rotor can also be designed such that a first proportion of the reinforcement elements/fibers, which is more than 30% of the reinforcement elements/fibers, in particular more than 50% of the reinforcement elements/fibers, has a length corresponding to at least 30%, in particular at least 50%, of the maximum height of the impeller elements, measured in the radial direction of the rotor in the expanded state. This results in stabilization forces which span larger parts of the rotor and stabilize this on the whole.

It can additionally be provided that the first proportion of the reinforcement elements/fibers in the operating state runs substantially perpendicularly to the axis of rotation. As a result of this orientation of the reinforcement elements/fibers, elongation stresses in the rotor that are produced by the load of the fluid to be conveyed can be taken up optimally.

Furthermore, the rotor can be designed such that the diameter of the reinforcement elements/fibers, in particular of the first proportion of the reinforcement elements/fibers, is less than 40 micrometers. By means of such a small diameter of the reinforcement elements/fibers, small bending radii can be achieved, such that the risk of breakage of the reinforcement elements/fibers is further reduced.

In addition, it can be provided that the surface of the reinforcement elements/fibers is provided with an adhesion promoter. A good anchoring of the reinforcement elements/fibers in the plastic material of the matrix is thus achieved, which leads to a further improvement of the take-up of elongation stresses by the reinforcement elements/fibers.

The invention additionally relates to a method for producing a rotor according to claim 1 or one of the following claims by means of a molding method, in particular an injection molding method, in which the material of the impeller elements is introduced into the volumes of the impeller elements in the radial direction with respect to the rotor axis in such a way that the molding material flows into the volume of each individual impeller element in the radial direction.

In a method of this type the molding material can be injected for example in the axial direction in the central region of the rotor, for example in the volume of a rotor hub, and can be distributed radially from there into the individual impeller elements. Each individual impeller element is then filled from the inside out in a radially directed direction of flow of the material. However, a filling from the radially outer ends of the impeller elements radially inwardly, in a manner directed towards the rotor axis, is also possible.

The reinforcement elements/fibers or also film portions, which for example can consist of glass, but also of carbon or polycarbonate or metal, provided in the molding material are entrained by the flow of the matrix material and are oriented primarily in the direction of flow of the material.

A mold optimized for the production of the described rotor and for the described method is also presented. This mold is characterized in that overflow channels are provided in the volumes of the impeller elements at the radially extending edges thereof in order to enable an uninterrupted flow of the molding material in the radial direction.

Due to the overflow channels provided at the edges, the formation of swirls with local backflows in the region of the edges of the impeller elements is prevented, such that a largely laminar flow can be formed. The reinforcement elements/fibers are thus embedded in the matrix in a predominantly stretched position. This is therefore expedient in particular since the mold enables a rotor to be molded in the second, expanded state, that is to say free from external stresses.

In addition to the overflow channels provided at the side edges of the impeller elements, overflow channels can also be formed in the mold at the radially outer ends of the volumes, which overflow channels allow the molding material to flow out at the radially outer ends of the impeller elements. The excess molding material can be removed once the rotor has solidified at least in part in the mold.

With regard to the arrangement of the reinforcement elements/fibers in the volume of the impeller elements, a spacing from the bending neutral plane might be desired purposefully in order to achieve a particular stabilization in a direction by stretching of the reinforcement elements/fibers when the impeller elements bend out in the event of the loading by the fluid counterpressure in the operating state. In any case, the reinforcement elements/fibers should run advantageously within the impeller elements and should maintain a specific minimum distance from the outer delimiting faces of the impeller elements.

A plurality of groups of reinforcement elements/fibers of different length can also be provided in the rotor, wherein at least one group has a specific minimum length, whereas the reinforcement elements/fibers of one or more groups are shorter or have a length distribution that has only a negligible number of reinforcement elements/fibers above a fiber length which is below a typical length of the first proportion of the reinforcement elements/fibers. The average length of the shorter reinforcement elements/fibers is typically less than a third of the length of the first proportion of the reinforcement elements/fibers.

The rotor can advantageously be designed such that each reinforcement element/each fiber of the first proportion of the reinforcement elements/fibers deviates in its course by at most 45° in the axial direction and/or azimuthal direction from a position aligned radially with the rotor axis (14). The reinforcement elements/fibers then run in a plane in which the entire axis of rotation of the rotor also runs, such that they can extend radially outwardly initially perpendicularly starting directly from the axis of rotation, for example. However, an orientation of the reinforcement elements/fibers from the axis of rotation radially at an angle between 45° and 90° to the axis of rotation is also possible. In one embodiment, the extent of the reinforcement elements/fibers at any rate does not have an azimuthal orientation (running in the peripheral direction) or only has a small orientation of this type.

The rotor can also be designed such that the impeller elements consist of a foam material. Here, a closed-pore foam material is envisaged in particular, which can be effectively stabilized by the reinforcement fibers and which can still be compressed easily and to a sufficient degree. Particularly in the case of a foam material, a deflection of the reinforcement elements/fibers in order to avoid dropping below a critical bending radius is possible particularly easily during the compression movement. Foam materials of this type usually have corresponding pores within the volume of the impeller elements, but are practically completely closed at the outer delimiting surfaces.

The rotor can also be formed in such a way that a proportion of reinforcement elements/fibers in the expanded state of the rotor runs transversely to the reinforcement elements/fibers of the first part and in particular encloses an angle therewith of at least 30° on average. The particular group of fibers can thus almost completely prevent a bending of the rotor or an impeller element of the rotor in the longitudinal direction of the fibers, provided the bending occurs in a direction in which the fibers are loaded by a tensile stress. If two directions are distinguished in the described manner by the different arrangement of two fiber groups, a three-dimensional form of the rotor or of part of the rotor can be stabilized very efficiently and strengthened against bending in various directions.

It can additionally be provided that the reinforcement elements/fibers are present at least in part in the form of fabric portions having fibers that run longitudinally and transversely. The fabric portions by way of example can extend in their longitudinal direction at least twice, three times, five times or ten times as far as in the transverse direction perpendicularly thereto, such that they form an elongate strip in each case. First fibers are then readily provided within this fabric in a longitudinal direction, and second fibers running transversely thereto are then readily provided perpendicularly or at an obtuse angle thereto.

By way of example, it can also be provided that the reinforcement elements are present in the form of film strips, of which the length is at least three times, in particular at least five times, more particularly at least ten times as great as their width. These film strips can consist of an anisotropic polymer, which for example has a much greater tensile strength in the longitudinal direction than in the transverse direction. However, they can also consist of an isotropic film, for example made of high-tensile plastic material or also made of a metal, such as aluminum, silver, titanium, nitinol, or gold.

In addition, it can be provided advantageously that the reinforcement elements are surrounded by the plastic from which the rotor is predominantly made, at least to a proportion of 90%, in particular 99% of their surface, and more particularly completely. In an individual case it can be that reinforcement elements in the injection mold contact the wall of the mold so that they appear at the outer surface of the rotor in the finished product. However, in the normal case, only the ends of the reinforcement elements are arranged in an exposed manner on the outside of the rotor, wherein even this is relatively unlikely due to the introduction of reinforcement elements and a suitable flow guidance of injection molding material during the injection molding process.

In the case of the rotor, it can additionally also be provided that the plastic material in which the reinforcement elements are embedded has different properties, at least in regions, on the side of the impeller elements not loaded by the fluid counterpressure during operation compared to the side of the impeller elements that is loaded by the fluid counterpressure, in particular is more heavily cross-linked or shrunk on the side not loaded by the fluid counterpressure or carries there, on the surface, a support shrunk on the impeller element, said support being provided in the form of one or more films, coatings or fibers. In this regard, the two sides of the reinforcement elements are intended to mean, in the volume of a particular impeller element, the volume regions on the two sides of the plane or surface constituting the bending neutral plane or surface under bending load.

One of the sought objectives of the invention is that the second state of the rotor, assumed by the rotor in the state free from external forces, differs to a minimal extent from the third state assumed by the rotor during operation as it rotates in a fluid under the action of the fluid counterpressure. It is therefore desirable that the reinforcement fibers already in the second state of the rotor are stretched to the greatest possible extent and run in a direction in which they delimit at least any bending of the rotor.

This can be assisted in that the form of the rotor in the second state, in which the rotor is free from forces, differs from the form assumed by the rotor in the injection mold. By means of suitable design of the plastic matrix formed by the injection molding material, it is possible that already in the state free from external forces a deformation occurs in the direction of the third state by means of resilient forces of the injection molding material, said deformation preloading the fibers. This effect can be achieved by way of example in that a material different from the reinforcement elements is provided in or on the rotor and brings the rotor, in particular the impeller elements, into a form in which the reinforcement elements are preloaded. Since, during the actual molding of the reinforcement elements in the matrix, these elements are more or less free from forces, this is achieved by a modification of the plastic matrix or of the body of the rotor on the whole after the completion of the injection molding process. By way of example, the plastic matrix can be treated in a particular manner following removal from the injection mold, in such a way that the material of the impeller elements is lengthened on the side subjected to the fluid counterpressure during operation or is shrunken or anisotropically shortened on the opposite side. This can be implemented by way of example by an irregular cross-linking of the plastic matrix, which is different on the two sides of the neutral fibers of the impeller elements. However, this can also be achieved by coating the impeller elements, on the side opposite the side of the impeller elements exposed to the fluid counterpressure during operation, with a film which shrinks or can be shrunk after the coating, for example by electron beam cross-linking or UV cross-linking or by thermal treatment.

A rotor for a compressible fluid pump which can be radially expanded and compressed between a first, compressed state and a second, expanded state can also be provided, wherein it can additionally be provided that one or more impeller elements of the rotor is/are produced by injection molding with simultaneous addition of reinforcement elements in the expanded state, wherein the reinforcement elements are surrounded on all sides by an injection molding material and are stretched at least sectionally in the expanded state, in particular are stretched to an extent of at least 90%, more particularly 95%, and more particularly 99% or, with use of a fabric, are stretched to the greatest possible extent.

By way of example, the rotor can also be designed in such a way that the reinforcement elements in the second, expanded state of the rotor without a fluid counterpressure are stretched to such an extent that they are lengthened upon transition to a third state, which constitutes the operating state with a fluid counterpressure, by less than 5%, in particular less than 1%, wherein the lengthening is measured in particular on the basis of the distance between the two ends of a reinforcement element before and during the tensile load.

By way of example, it can also be provided in the case of the rotor that in a second, expanded state of the rotor and/or a third operating state with fluid counterpressure, at least a proportion of the reinforcement elements, in particular at least 10%, more particularly at least 30%, run in a stretched and straight manner, at least in a region of an impeller element in which said impeller element is curved.

It can additionally be provided that, in a region of an impeller element in which this is curved, at least two proportions of reinforcement elements run in a straight and stretched manner, wherein the directions in which the reinforcement elements run are parallel within the same proportion, but are different between the two different proportions. The fibers within the various groups can be introduced into the injection mold already connected to one another in the form of a fabric or can be introduced into the injection mold separately from one another, in particular in succession.

A further embodiment of the rotor can provide that the length of the reinforcement elements, in the case of at least 30%, in particular at least 50% of the elements, is greater than the average thickness of the impeller elements, in particular at least twice as long, more particularly at least five times or ten times as long. The reinforcement elements of such length can be supplemented when filling the molding material by other filling elements, for example very short fibers and/or particles, wherein the short fibers can also be present in stretched form. However, this has little effect in respect of a delimitation of the curvature of the rotor, since these fibers are usually very short. In this regard, the thickness of the impeller elements at any point of the impeller elements means the extent in the direction in which the extent of the impeller element is smallest.

A further embodiment of the rotor can provide that reinforcement elements, in particular fibers, are introduced in an injection molding method into the plastic in which said reinforcement elements are embedded and have a sectionally curved course along the flow of the plastic into the injection mold during the time for which the rotor is disposed in the injection mold.

The invention additionally also relates to an injection mold for a rotor of the above-described type, with overflow channels provided in the volumes of the impeller elements at the radially running edges thereof in order to enable an uninterrupted flow of the molding material in the radial direction.

A method for producing the above-described rotor can provide that the material of the impeller elements is introduced into the volumes of the impeller elements in the radial direction with respect to the rotor axis in such a way that the molding material flows into the volume of each individual impeller element in the radial direction.

Due to the arrangement and size of the overflow channels of the casting mold, the flow direction of the inflowing molding material and therefore the orientation of the fibers along the flow can additionally be controlled.

A further method for producing a rotor can provide that the rotor is produced by molding, in particular injection molding, wherein the injection molding process is performed in two successive phases with different injection directions and/or from two different injection points. Reinforcement elements/fibers that run in groups in different directions can thus be introduced in a targeted manner into the injection molding material In a method for producing a rotor, it can also be provided that the rotor is subjected after the injection molding to a treatment that causes a different shrinking and/or cross-linking of the molding material on the side of the impeller elements loaded by the fluid counterpressure during operation compared to the opposite side. The rotor can thus be preloaded by production of internal stresses in such a way that it already assumes the third state, i.e. an operating state, which is stable, when the rotor is exposed to a fluid counterpressure, without influence of external forces. This is implemented in that the internal stresses are directed and dimensioned in such a way that as a result the reinforcement elements are already loaded by a tensile force which lies in the order of the forces to which the reinforcement fibers are exposed during operation of the rotor.

By way of example, it can also be provided that a shrinkable or shrinking layer is applied to at least one of the impeller elements on the side opposite the side of the impeller elements exposed during operation to a fluid counterpressure.

Alternatively or additionally, it can be provided by way of example that at least two different injection openings are provided in the injection mold for the injection molding material. The flow of the injection molding material in the mold can thus be altered in a targeted manner during the molding process, such that, with addition of reinforcement elements in various phases, the reinforcement elements can be arranged in each case in the primary flow direction of the injection molding material and therefore in different directions in accordance with the various phases of the injection molding process. For this purpose, by way of example, a first quantity of the injection molding material can be injected through a first injection opening and a second quantity can be injected through a second injection opening in succession or simultaneously or in a variable proportion to one another.

The innovation will be presented and explained hereinafter on the basis of exemplary embodiments in drawings, in which FIG. 1 schematically shows a sectional view of a catheter pump which is introduced into the chamber of a patient's heart, FIG. 2a shows a detail of a rotor of a catheter pump for conveying blood, FIG. 2b shows a cross-sectional illustration of a relaxed rotor with a fiber illustrated by way of example, FIG. 2c shows the cross-sectional illustration of a rotor in the third state, that is to say the operating state, FIG. 2d shows the cross-sectional illustration of a rotor in the compressed state, FIG. 2e shows a cross-sectional illustration of an impeller element with marking of the bending neutral plane and with reinforcement fibers illustrated by way of example, FIG. 3 shows a schematic illustration of a plane containing the axis of rotation of the rotor, FIG. 4 shows a detail of a planar impeller element with a fiber for reinforcement, FIG. 5a shows the orientation of a fiber during the molding process, FIG. 5b shows a side view of the portion from FIG. 4, FIG. 6 shows the portion of an impeller element as shown in FIGS. 4 and 5 after a buckling process, FIG. 7 shows a schematic view of a molding tool for a rotor, wherein the molding process is indicated by flow arrows, FIG. 8 shows a mold for a rotor with an injection direction opposite that in FIG. 7, FIG. 9 shows a mold in which measures have been taken to prevent a swirling of the injection molding material in the volume of the impeller elements, FIG. 10 shows a further mold, FIG. 11 shows a film-like, strip-shaped reinforcement element, FIG. 12 shows a fabric-like reinforcement element, and FIG. 13 shows a cross-section through an impeller element, FIG. 14a shows a fabric formed of fibers in a state free from forces, FIG. 14b shows the fabric from FIG. 14a in a maximally stretched state under load, FIG. 15a shows an impeller element in a perspective view in the expanded state without action of external force, FIG. 15b shows a sectional view of the impeller element from FIG. 15a in the plane of section denoted there by A-A, FIG. 16a shows an impeller element in a perspective view in the expanded state without action of external force, FIG. 16b shows a sectional view of the impeller element from FIG. 16a in the plane of section denoted there by B-B, FIG. 17a shows an impeller element in a side view in the expanded state without action of external force, and FIG. 17b shows a sectional view of the impeller element from FIG. 17a in the plane of section denoted there by C-C.

FIG. 1 shows, in cross-section, the heart 1 of a patient with a plurality of heart chambers, wherein the heart chamber 2 is connected to the aorta 12. A catheter 4 is advanced into the heart chamber 2 through the aorta 12, wherein a pump head 3 with a rotary pump is arranged at the end of the catheter 4. The rotary pump can be driven by means of a rotatable shaft 6 running through the catheter 4, which shaft is connected within the pump head 3 to a pump rotor 42. The pump rotor rotates in a housing (not illustrated in greater detail) of the pump head 3.

The flexible shaft 6 is connected to a motor 7, which for example is arranged outside the patient's body. The torque can be transferred for example by means of a magnetic coupling from the motor 7 in both directions of rotation 8, 9 to the shaft 6.

The catheter 4 is usually advanced via a port from outside the body, through the skin and tissue and also the vessel wall, into the aorta 12 and therein.

The pump sucks in blood in the heart chamber 2 and conveys it into the aorta 12. The heart pump can thus either assist the function of the heart 1 or replace it at least temporarily.

Besides the catheter pump with mechanical drive illustrated in the drawing, other pumps, in particular for intracorporeal use, also form the subject of this patent, for example pumps with hydraulic or electric drive, including pumps in which the drive is within the human body.

The pump, together with the pump head, the pump housing and the rotor, is radially compressed for displacement in the aorta and is displaced for example within the catheter 4. The pump can then be slid out axially from the catheter 4 and can radially unfold, i.e. can be expanded. During this process, high demands are placed on the materials of the pump housing and in particular the pump rotor: The impeller elements of the pump rotor have a very thin wall thickness, but must still remain dimensionally stable and convey blood reproducibly, even at high rotational speeds.

For this purpose, reinforcement fibers (fibers) are embedded in the matrix of the plastic from which the rotor is made and for example can be provided as glass fibers or polycarbonate fibers. Such reinforcement elements/fibers are illustrated in FIG. 2a in three individual examples. The three reinforcement elements/fibers 10, 11, 13 are shown, each of which has a first end or a first portion 10a, 11a, 13a, which is closer to the axis of rotation 14 than the second end/the second portion 10b, 11b, 13b of said reinforcement elements/fibers 10, 11, 13.

The reinforcement elements/fibers 10, 11, 13 extend substantially radially outwardly away from the axis of rotation or a point in the vicinity of the axis of rotation 14 of the rotor. Here, it is not necessary for the rotor 42, as in the illustrated example, to have a hub 43. The spiraled impeller element 15 can also have an inherent stability such that a rotor hub is not necessary.

In principle, the plastic matrix of the impeller element or the impeller elements 15 can be reinforced with reinforcement elements/fibers, which are distributed and arranged irregularly in respect of length and/or thickness and/or orientation. One aspect is that a certain minimum proportion of the reinforcement elements/fibers in the expanded state of the rotor, which is illustrated in FIG. 2b, runs in a substantially stretched manner away from the axis of rotation. In the operating state, which corresponds to the third state and which is illustrated in FIG. 2c, these reinforcement elements/fibers are stretched and are additionally subject to a tensile stress, which is produced by the load of the conveyed liquid. This tensile stress, however, does not lead to a noticeable lengthening due to the longitudinal strength of the reinforcement elements/fibers and therefore also leads to hardly any change of form of the rotor compared to the stress-free expanded state or does not lead to any further deformation above a specific operating point. The proportion of the reinforcement elements/fibers that meets the aforesaid condition in the total amount of reinforcement elements/fibers embedded in the plastic of the rotor should be at least 30% or advantageously 50% or even more advantageously for example 70%, measured in percent by volume or mass of the reinforcement elements/fibers or also on the basis of the number of reinforcement elements/fibers. Here, a certain minimum length of the reinforcement elements/fibers is advantageously given, for example approximately at least 20% or at least 40% or 50% of the radius of the rotor. The reinforcement elements/fibers can change easily during the filling of the mold from the axial orientation, corresponding to the filling direction axially into the hub 43, into the radial position of the impeller elements 15 without being bent for this purpose, since the angle between the impeller element 15 and the hub 43 runs relatively flat at <30° or preferably <20°. The reinforcement elements/fibers, during the radial filling of the impeller elements 15, are thus easily entrained by the surrounding matrix and are oriented radially with the material flow in the impeller element, according to FIG. 2a.

Further advantageous properties of the reinforcement elements/fibers are a specific maximum thickness, wherein a diameter of at most 40 μm can be advantageous in order to produce no breakage of the reinforcement elements/fibers in the event of a strong bending of said reinforcement elements/fibers. By contrast, with a measurement of approximately 40 μm, the reinforcement elements/fibers are flexurally rigid enough to return the matrix surrounding them back into the starting state following deformation and to prevent a long-term creep of the matrix under permanent bending load. Reinforcement elements/fibers with a diameter of 40 μm are also resistant to compressive and tensile stresses, such that, with an arrangement outside the bending neutral region, they also produce a restoring moment and act against a remaining deformation.

The reinforcement elements/fibers can be coated with an adhesion promoter in order to improve the connection to the matrix.

FIG. 2b shows, in cross-section, a rotor 42' with impeller elements 15', 15" in the relaxed, expanded state. The reinforcement elements/fibers 55, 56 in this state have a maximally stretched form, such that they resist any further deformation of the rotor on account of their longitudinal rigidity.

The arrow 57 shows the direction of rotation of the rotor in the operating state. The arrows 58, 59 show the load acting on the impeller elements 15', 15", i.e. the fluid counterpressure acting on the impeller elements as a result of the conveying movement. FIG. 2b shows the chord 60, which denotes the height of the impeller element 15' as measured in the radial direction from the axis of rotation.

The chord 60 is also shown in FIG. 2c, which shows the rotor 42' in the third state, that is to say the operating state. The reinforcement fibers 55, 56 are under tensile stress due to the load 58, 59 and absorb the strains into the impeller elements 15', 15". The length of the chord 60, that is to say the height of the impeller elements, remains constant in the operating state compared to the second state or increases by a small amount, but does not become smaller.

FIG. 2d shows the rotor 42' in compressed form, in which the impeller elements are folded against the rotor hub. In this position, the pump can be brought through a narrow channel to the site of operation.

FIG. 2e shows a detailed view of an operating state of the impeller element 15' in cross-section. The "bending neutral fiber" or "bending neutral plane" is illustrated by the dashed line 61, that is to say the line or surface that under load experiences neither an elongation nor a compression as the impeller element 15' is bent. A plurality of reinforcement fibers, denoted by way of example by 62, 63, lies on the side of the line/plane 61 on which an elongation stress is created in the operating state. The reinforcement elements/fibers are sectionally stretched there and run straight and also substantially parallel to the line/plane 61. As a result, they can effectively take up elongation stresses.

The possible orientation of the reinforcement elements/fibers will be explained in greater detail on the basis of FIG. 3. The rotor hub is denoted in FIG. 3 by 16, and the axis of rotation is denoted by 14. A plane 17 on the basis of a cut rectangle is illustrated, wherein the plane 17 contains the axis of rotation 14, that is to say the axis of rotation 14 runs completely in the plane 17. It should be noted that this illustration is simplified, since the impeller elements are usually spiraled, such that the plane 17 is then no longer flat, but instead curved.

Two reinforcement elements/fibers 18, 19 have been shown by way of example and both run in the plane 17 substantially radially with respect to the axis of rotation 14. The fiber 18 runs at an angle α to the axis of rotation 14, partially in the axial direction, wherein the angle α is advantageously between 45° and 90°. The fiber 19 is oriented in such a way that it is arranged at right angles to the axis of rotation 14. An actual blade is curved in a spiraled manner in three dimensions, such that in many cases a limited extent of the reinforcement elements/fibers is added in the azimuthal direction.

The individual reinforcement elements/fibers do not have to be positioned in such a way that their first start point/end point is in the region of the axis of rotation 14 or the rotor hub 16. They can also be arranged such that they run between two end points which are both radially distanced from the rotor axis 14 and/or from the rotor hub 16. However, they can also extend from a first radially outer blade edge to at most a second, radially opposite blade edge, in any case beyond the axis.

A detail 20 of an impeller element is illustrated schematically in FIG. 4, wherein the detail 20 is cuboidal. A fiber 19 is illustrated in the portion 20.

FIG. 5a clarifies how the central orientation of the fiber 19 is achieved. The preferably laminar flow profile when filling the mold between the delimiting walls 53 and 54 has the fastest flow speed in the middle and the slowest speed in the vicinity of the walls. The fiber 19, which is initially skewed, is illustrated in three angular positions reached successively from left to right and is drawn by the material flow, indicated by the arrows 50, 51, in the direction of the middle of the flow profile as a result of the speed distribution in the mold. The speed distribution of the flow is illustrated in the graph 52 of the diagram with the axes x ($\Delta$ speed) and y ($\Delta$ location coordinate in the mold).

FIG. 5b shows a side view, wherein the material of the portion 20 has been illustrated transparently, such that the course of the fiber 19 approximately in the middle between the delimiting faces of the impeller element is visible.

The behavior of the fiber under heavy bending or buckling of the impeller element will be described on the basis of FIG. 6.

FIG. 6 shows the portion 20 of the impeller element after buckling. The fiber 19 is also deformed. Due to a certain inherent rigidity of the fiber, however, this can push outwardly in the direction of the arrow 21 in the event of the buckling due to the resilience of the material of the impeller element so as to achieve a greatest possible radius of curvature of the fiber and thus counteract a breakage of the fiber. In the region of the buckling point, the fiber 19 is therefore deflected from the middle between the delimiting walls of the impeller element for the duration of the buckling. In FIG. 6 the central plane of the impeller element has been illustrated at least in part by a dashed line 22 for the sake of clarity. In order to achieve this effect, a softness of the plastic matrix of the rotor is advantageous, corresponding to a Shore hardness <100 D, in particular <80 D.

The design according to the invention of a molding tool/a mold for a rotor according to the invention will be discussed on the basis of FIG. 7.

FIG. 7 shows a longitudinal section of the injection mold, wherein the region comprising the volume of the rotor hub is denoted by 23 and the volumes of the individual impeller elements are denoted by 24, 25, 26 and 27. In addition, an injection direction is indicated in FIG. 7 by the arrow 28. The further arrows 29, 30, 31, 32, 33 indicate that the injection molding material flows in axially along the axis of rotation 14 of the resultant rotor and from there flows radially outwardly into the volumes of the impeller elements. By way of example, the longitudinal axis of one of the impeller elements has been indicated by a dot-and-dash line and denoted by 44. If reinforcement elements/fibers of appropriate length are introduced in sufficient number into the injection molding material, these reinforcement elements/fibers will be oriented in accordance with the primary flow direction of the material and will remain in place as the material solidifies.

Displaced air and excess molding material can flow out at the radially outer ends of the impeller elements through openings 45.

In FIG. 8 an opposite injection direction is indicated, wherein the injection molding material is injected radially inwardly from the radially outer ends 34, 35 of the impeller elements to the volume of the rotor 23. In this case as well, long reinforcement elements/fibers can also be introduced, which are oriented and arranged in the manner and way intended in accordance with the invention.

On the basis of FIG. 9, it is shown that in the case of narrow impeller elements 36, 37 the molding compound flowing radially from the inside out is swirled at the edges 38, 39 of the volume of a specific impeller element by friction, such that there is no laminar flow of the molding material created as said material flows in.

On the left-hand side in the illustration of FIG. 9, a mold variant is illustrated, which in the region of the edges 40, 41 has overflow openings or overflow slots, through which some of the injection molding material can flow out in the axial direction of the rotor, such that the swirling illustrated on the right-hand side of FIG. 9 is eliminated. In the central region of the impeller element 37, a quasi-laminar flow is thus created, such that the introduced reinforcement elements/fibers can arrange themselves there in stretched form in a region around the "neutral fibers" or neutral plane (under the bending load occurring during pump operation) without being deformed by influencing of the flow with the injection molding material. Once solidified, the parts of the injection molding material that can exit through the openings at the edges 40, 41 of the volumes of the impeller elements in the injection mold are removed, for example by being cut off. The situation can be the same at the outer edges of the impeller elements, as in FIG. 7. Here, two overflow channels 45 are provided, through which the plastic without reinforcement elements/fibers can escape.

Due to an asymmetric distribution of the outflow openings, for example a larger outflow cross-section in the vicinity of the region of the impeller element exposed to the fluid counterpressure of the liquid during operation, there is a stronger flow there of the molding material, such that more reinforcement elements/fibers are embedded there than on the side opposite the "neutral plane", with the result that the elongation stresses can be taken up by a high number of reinforcement elements/fibers.

FIG. 10 schematically shows an injection mold 70 with a first injection opening 71 and a second injection opening 72, wherein the two injection openings 71, 72 are arranged at mutually opposed ends of the central cavity 73, in which the hub of the rotor is formed by the molding process. The cavities in which the impeller elements are created have been indicated only very schematically and have been denoted by 74 and 75. The arrows 76, 77 denote the flow directions of the plastic flowing into the mold. If the plastic is injected successively or in alternating proportions through the first injection opening 71 and the second injection opening 72 into the mold, different flow directions of the liquid molding material are thus created. If the reinforcement elements are added hereto, different orientations of the reinforcement elements in the produced rotor also result accordingly. In this way, different orientation patterns can be provided by controlling the injection speed through the injection openings and by changing the injection speeds or the ratio of the injection speeds through the various injection openings during the molding method.

A perspective view of a reinforcement element in the form of a metal foil or a plastic film 78 is illustrated in FIG. 11, which foil/film by way of example can be just a few micrometers thick, a few tenths of a millimeter wide, and a few millimeters long.

The cover face opposite this side or cover face 83 is denoted by 85. In the illustrated example a coating 86 is provided on this side of the impeller element 82 and can be provided by a glued-on film or a liquid coating, for example a varnishing.

What is known as the neutral "fiber" or plane in the sense of mechanics in the event of a bending of the impeller element 82 during pump operation is shown in a dashed manner and has been denoted by 87.

Figure 1:
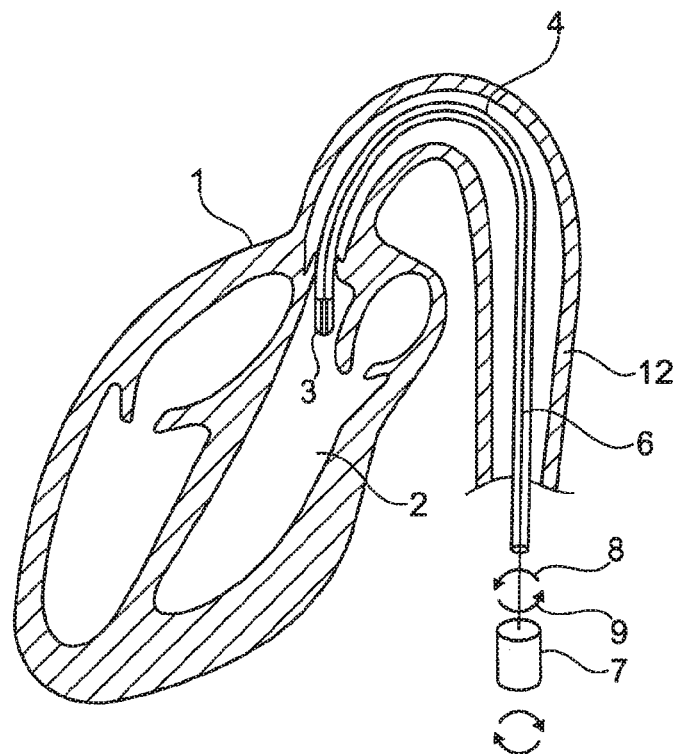
Figure 2A:
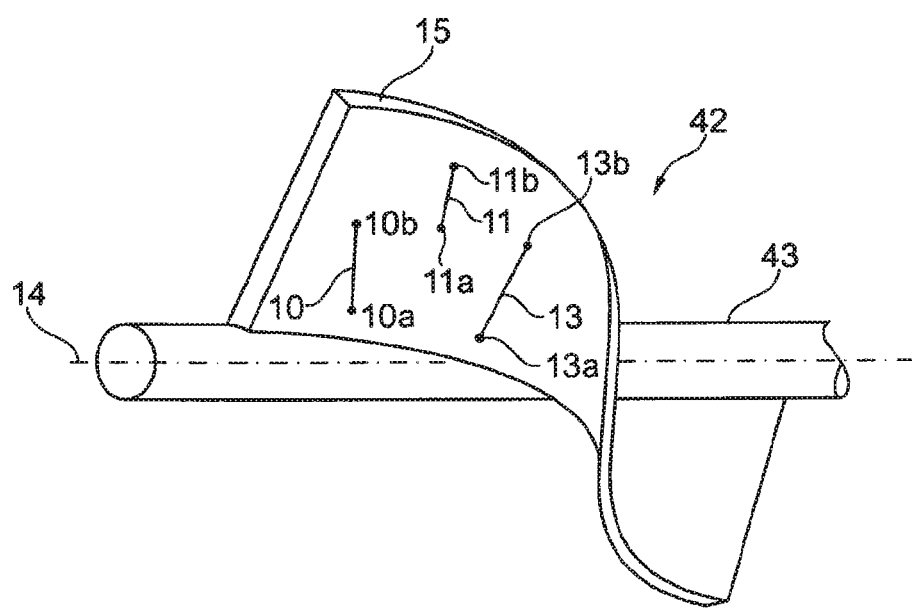
Figure 2B:
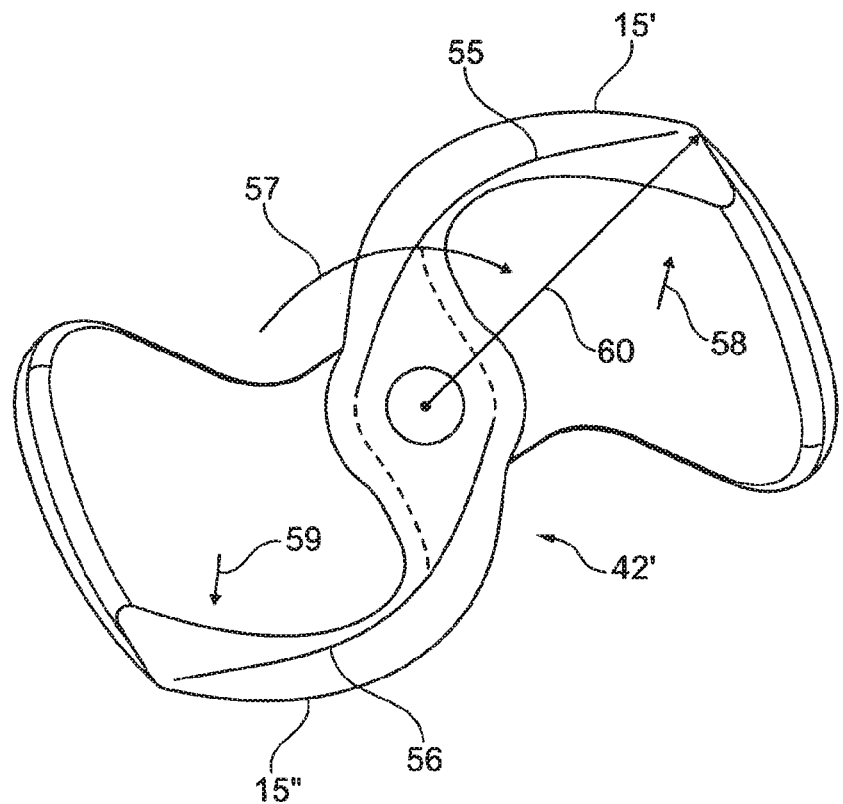
Figure 2C:
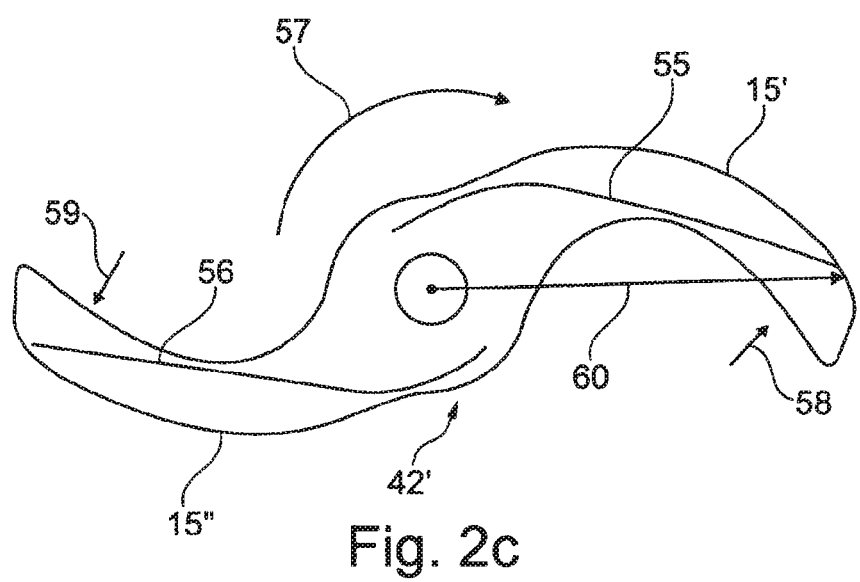
Figure 2D:
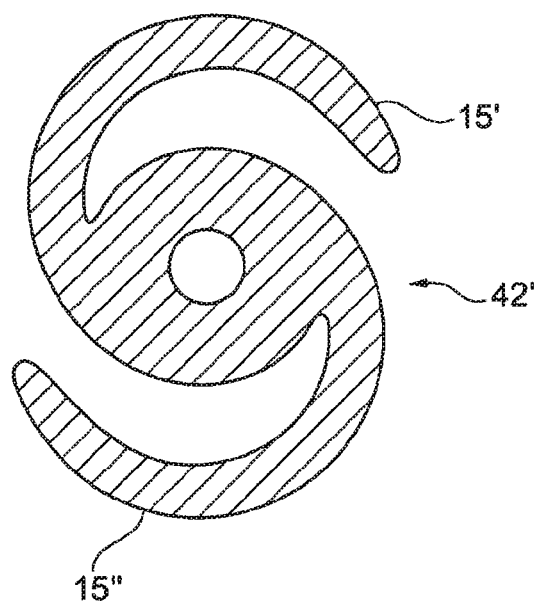
Figure 2E:
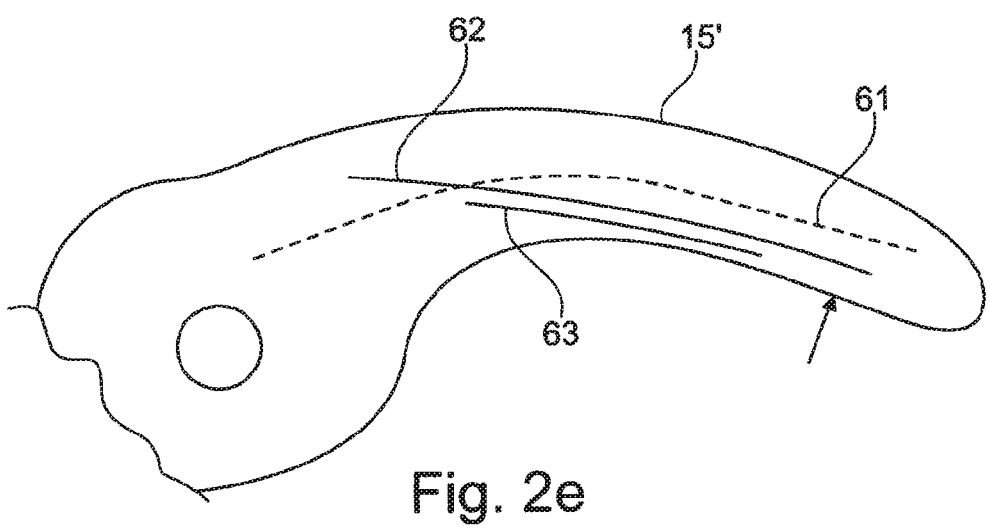
Figure 7:
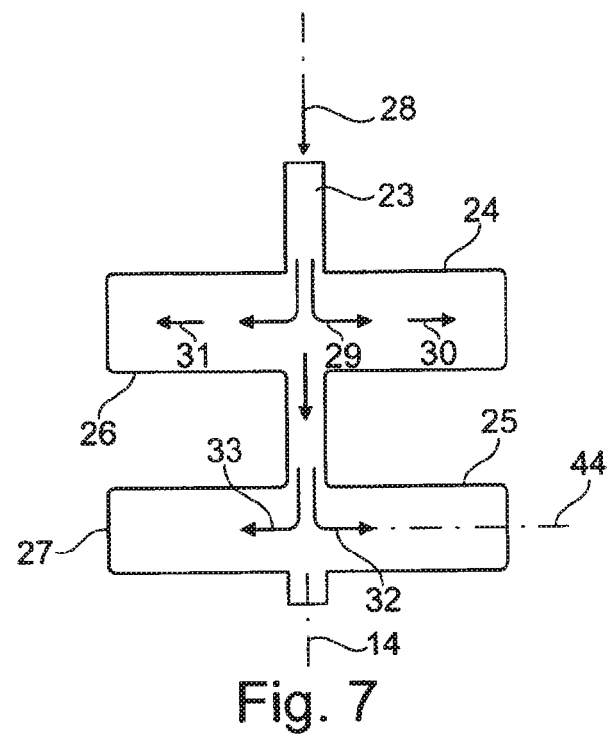
Figure 8:
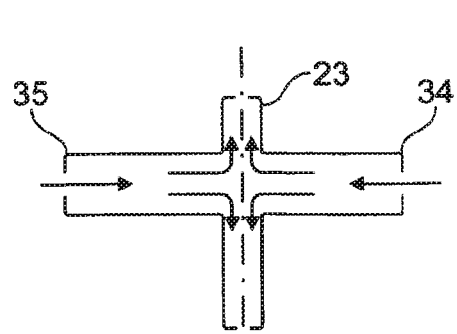
Figure 9:
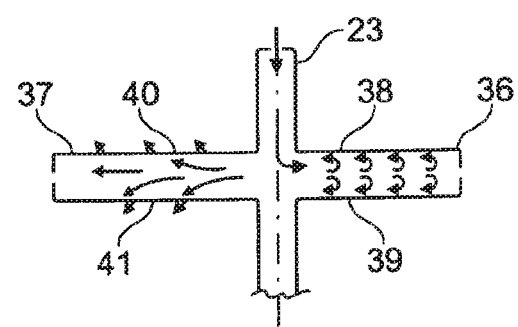
Figure 10:
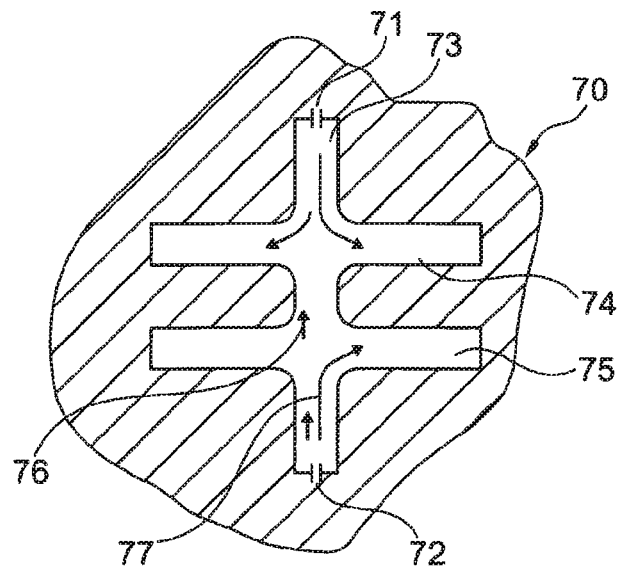
Figure 11:
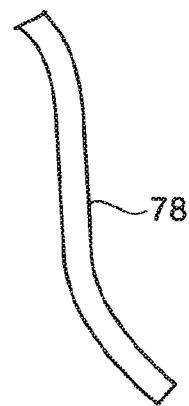
Figure 12:
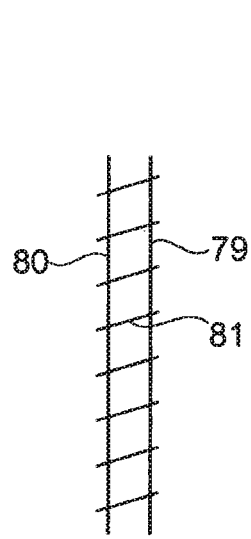
FIG. 12 shows, as reinforcement element, an elongate fabric strip, which schematically has only two fibers 79, 80 running in the longitudinal direction and a multiplicity of shorter fibers 81 running transversely thereto. A fabric of this type can take up tensile forces particularly well in both longitudinal directions of the fibers present.
Figure 13:
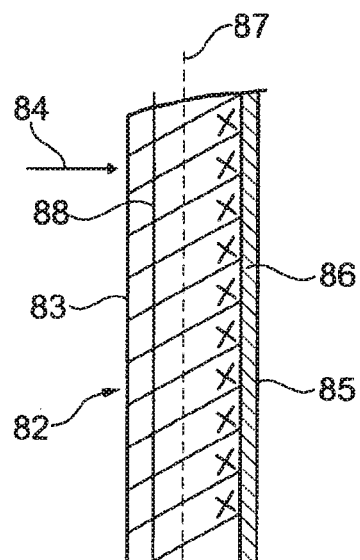
FIG. 13 shows a region of an impeller element 82 schematically in cross-section. Here, 83 denotes the cover face that lies on the pressure side during operation and that is exposed to the fluid counterpressure, indicated by the arrow 84.

If it is assumed that the impeller element, as illustrated in FIG. 13, is in the state free from forces, that is to say no external forces are acting on the impeller element, it can be provided that in this state the reinforcement elements, of which one has been shown by way of example and denoted by 88, are present in a stretched form and free from forces.

If, by the action of the fluid counterpressure 84, a bending force is applied to the impeller element in the direction of the arrow 84 upon rotation of the rotor in a fluid, the reinforcement elements 88 are subjected to tensile loading, since an elongation occurs on the side of the neutral fibers 87 arranged on the left in the drawing as a result of the bending of the impeller element. This bending is limited by the reinforcement elements 88 since these are practically stretch-resistant.

In order to further reduce the difference in form of the rotor between the second state free from forces and a third state, i.e. the loaded state, it can be provided that in the state free from forces, that is to say without any action of external forces on the rotor, the reinforcement elements 88 are already preloaded by internal material stress. This is achieved in that, after production of the rotor, more specifically once the injection molding process is completely finished, the impeller element is either stretched on the side of the cover face 83 or is shrunk on the side of the cover face 85.

This is achieved by way of example in that a coating 86 is applied to the cover face 85 after the injection molding process or during the injection molding process, for example by impregnation of the injection mold, which coating can be shrunk during the drying or cross-linking or by a subsequent treatment, in particular radiation cross-linking, UV cross-linking, or thermal treatment. The radiation cross-linking by way of example can also be introduced by means of one or more laser beams and thus can be locally applied in a very focused manner.

However, it is also conceivable that, additionally or alternatively to a cover layer 86, the material of the impeller element 82 on the side of the neutral plane of the fibers 87 facing towards the cover layer 85 is shrunk, for example by means of a heat treatment or by means of a cross-linking/polymerization, which does not take place on the other side of the impeller element or takes place there only to a lesser extent.

Figure 14A:
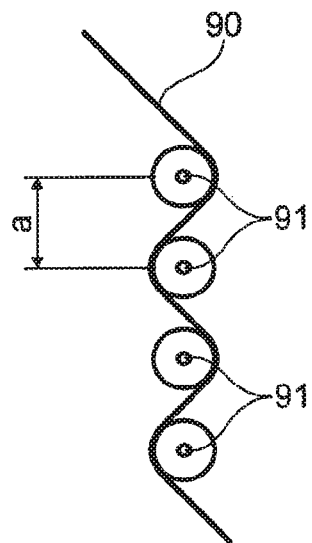
Figure 14B:
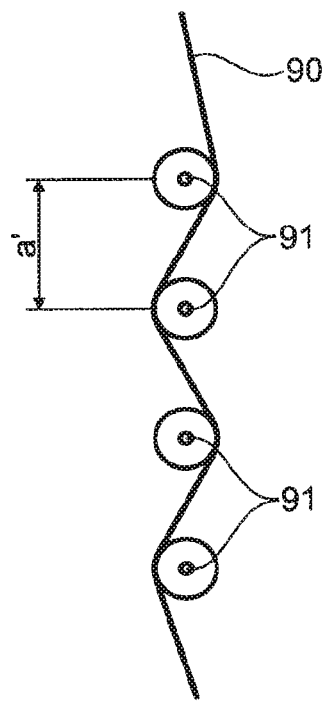

FIGS. 14a and 14b show, by way of example, a fabric formed of fibers. Here, the fiber 90 runs as part of a fiber bundle at an angle to further fiber bundles 91, wherein the fiber bundles 91 are arranged perpendicularly to the plane of the drawing and the fiber 90 passes the fiber bundles 91 on the left-hand and right-hand side in alternation. In FIG. 14a, which represents the relaxed state of the rotor, the fiber bundles 91 are arranged at a distance a from one another and the fiber 90 has a course that is curved back and forth. In FIG. 14b, which represents the state of the rotor during operation, the fiber bundles 91 are arranged at a greater distance a' from one another and the fiber 90 has a course that is curved to a lesser extent. It is clear from FIGS. 14a and 14b that a system of this type is already substantially stabilized before a complete stretching of the fiber 90 is achieved, since, beyond the state of FIG. 14b, the fiber bundles 91 would have to move at right angles to the fiber 90 in the basic material, which is fundamentally prevented thereby and by the fiber 90.

Figure 15B:
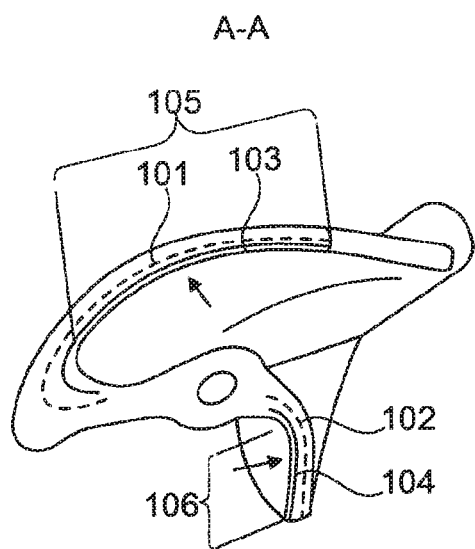
Figure 15A:
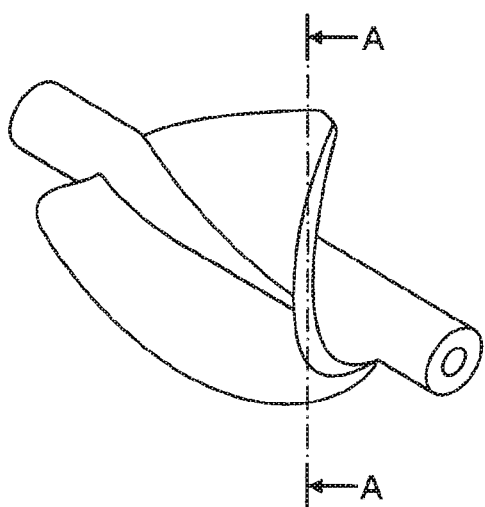

FIG. 15a shows a rotor in an expanded state free from forces in a perspective view and also denotes a plane of section A-A. FIG. 15b shows the same rotor in a sectional view along said plane of section. The dashed lines 101 and 102 represent the neutral fibers or surface of the respective blades. The fibers 103 and 104 show, by way of example, the course of two fibers in the illustrated planar section. The fibers are curved in this state. In the operating state under load, a pressure acts on the blades in the direction of the illustrated arrows on account of the fluid, whereby said blades open out further. Under full operating load, the fibers 103 and 104 are stretched at least in the regions denoted by 105 and 106 respectively, whereby a further opening out of the blades is prevented, since the very high-tensile fibers would then have to be stretched in their axial extent. The advantage of such a design is that the form of the blade is practically constant above a minimum rotational speed.

Figure 16B:
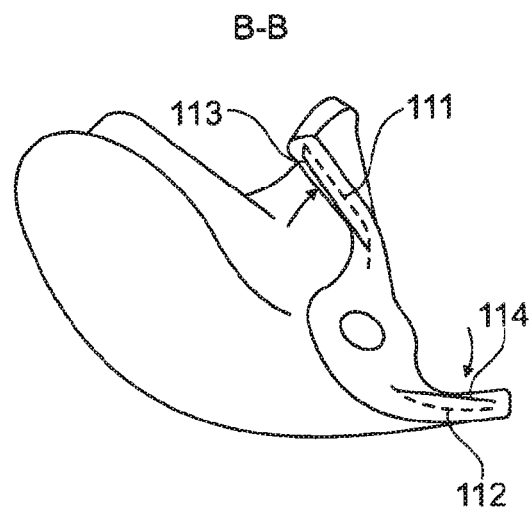
Figure 16A:
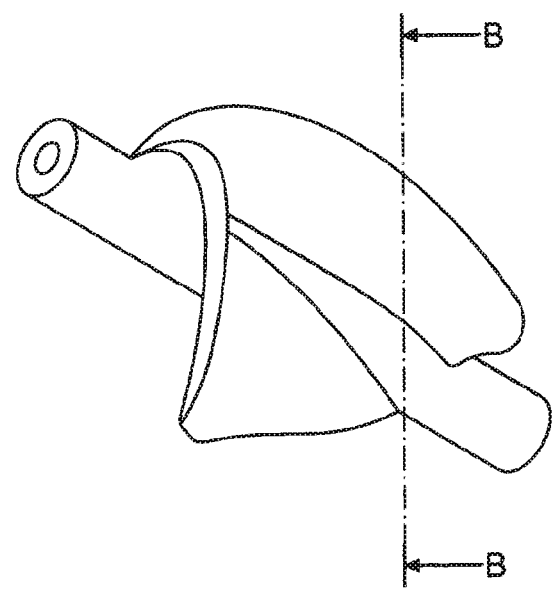

FIG. 16a shows a rotor in an expanded state free from forces in a perspective view and denotes a plane of section B-B. FIG. 16b shows the same rotor in a sectional view along said plane of section. The dashed lines 111 and 112 represent the neutral fibers or surface of the respective blades. The fibers 113 and 114 show, by way of example, the course of two fibers in the illustrated plane of section. As can be seen, the fibers in this example are already stretched to a great extent. Since the fibers are very high-tensile, a further elongation of the fibers is hardly possible. Even under the forces that occur in the operating state, which act on the blades due to the flow pressure and which are illustrated in FIG. 16b by arrows, such a blade will not significantly deform further, with the advantage that the blade form remains practically unchanged over practically the entire range of rotational speed.

Figure 17B:
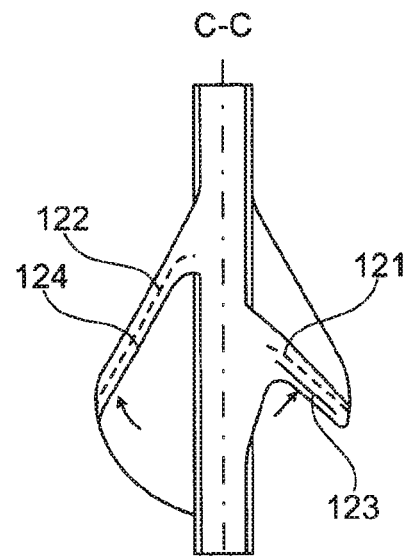
Figure 17A:
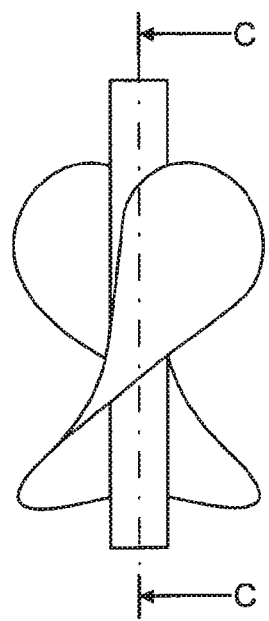

FIG. 17a shows a rotor in an expanded state free from forces in a view from the side with illustration of a plane of section C-C. FIG. 17b shows the same rotor in a sectional view along said planar section. The dashed lines 121 and 122 represent the neutral fibers or surface of the respective blades. The fibers 123 and 124 show, by way of example, the course of two fibers in the illustrated planar section. As can be seen, the fibers in this example are already stretched in a wide area. Since the fibers are very high-tensile, a further elongation of the fibers is hardly possible. Even under the forces that occur in the operating state, which act on the blades due to the flow pressure and which are illustrated in FIG. 17b by arrows, such a blade will not significantly deform further.

As a result of the above-mentioned features, in particular as a result of the design of the rotor and introduction of suitable reinforcement elements/fibers, a stable design of a rotor with sufficient form accuracy is achieved, even after partial overstretching or frequent alternating load or constantly applied bending load. As a result of the explained production method and the presented injection mold, an expedient and advantageous possibility for production of the presented rotor has been demonstrated.

The invention additionally comprises the following aspects, which can also be protected in each case individually and independently:

1st aspect: A rotor for a compressible fluid pump, in particular a blood pump which can be introduced through a blood vessel into a patient's body, which rotor has one or more impeller elements (15) and can be radially compressed and expanded between a first, compressed state and a second, radially expanded state, and consists at least in part of a plastic reinforced by strand-like reinforcement elements, in particular fibers, and is intended to rotate about an axis of rotation, wherein the rotor is tensioned in the first, compressed state and is free from external stresses in the second, expanded state, and wherein a third state exists, which the rotor (42) assumes in the operating state under load, wherein various materials of the rotor and their distribution are adapted to one another in such a way that, in the second state of the rotor, material stresses are produced selectively, which tension and/or stretch the reinforcement elements.

2nd aspect: The rotor according to aspect 1, wherein it is additionally provided that the reinforcement elements are surrounded by the plastic from which the rotor is predominantly made, at least to a proportion of 90%, in particular 99% of their surface, more particularly completely.

3rd aspect: The rotor according to aspect 1 or 2, wherein it is additionally provided that the plastic material in which the reinforcement elements are embedded has different properties, at least in regions, on the side of the impeller elements not loaded by the fluid counterpressure during operation, in particular on the corresponding side of the impeller element with respect to the fiber or surface constituting the bending neutral fiber or plane during pump operation under bending load, compared to the side of the impeller elements that is loaded by the fluid counterpressure, in particular is more heavily cross-linked or shrunk on the side not loaded by the fluid counterpressure or carries there, on the surface, a support shrunk on the impeller element, said support being provided in the form of one or more films, coatings or fibers.

4th aspect: The rotor according to aspect 1, 2 or 3, wherein it is additionally provided that one or more impeller elements of the rotor is/are produced by injection molding with simultaneous addition of reinforcement elements in the expanded state, wherein the reinforcement elements are surrounded on all sides by an injection molding material and are present in a stretched form at least in part in the expanded state, in particular are present in a form stretched to an extent of at least 90%, more particularly 95%, more particularly 99%.

5th aspect: The rotor according to aspect 1, 2, 3 or 4, in which it is additionally provided that the reinforcement elements in the second, expanded state of the rotor, without a fluid counterpressure, are present in a form stretched to such an extent that when transitioning to a third state, which constitutes the operating state with a fluid counterpressure, they are lengthened by less than 5%, in particular less than 1%, wherein the lengthening is measured in particular on the basis of the distance between the two ends of a reinforcement element.

6th aspect: The rotor according to aspect 1, 2, 3, 4 or 5, wherein it is additionally provided that in a second, expanded state of the rotor and/or a third operating state with fluid counterpressure at least a proportion of the reinforcement elements, in particular at least 10%, more particularly at least 30%, run in a stretched and straight manner in at least one region of an impeller element in which said impeller element is curved.

7th aspect: A method for producing a rotor for a fluid pump, in particular according to the first aspect, wherein it is provided that the rotor, after the injection molding, is subjected to a treatment which causes a different shrinkage and/or cross-linking of the molding material on the side of the impeller elements loaded by the fluid counterpressure during operation than on the opposite side.

8th aspect: A method for producing a rotor for a fluid pump, in particular according to the first aspect, by injection molding, wherein it is provided that a shrinkable layer is applied to at least one of the impeller elements on the side opposite the side of the impeller elements exposed to a fluid counterpressure during operation.

9th aspect: A mold for a rotor for a fluid pump comprising impeller elements according to the first aspect, in which mold at least two different injection openings are provided.

10th aspect: The rotor according to any one of the preceding aspects, wherein it is provided that the reinforcement elements have a two-dimensional extent, for example are embodied as film pieces or fabric with groups of fibers crossing one another (see FIGS. 14a and 14b).

The invention claimed is:

1. A rotor for a compressible fluid pump which can be introduced through a blood vessel into a patient's body, the rotor comprising:
   one or more impeller elements,
   wherein the rotor is configured to be radially compressed and expanded between a compressed state and an expanded state, the rotor further comprising, at least in part, a plastic material reinforced by strand-like reinforcement elements,
   wherein the rotor is intended to rotate about an axis of rotation, and
   wherein the rotor is tensioned in the compressed state and is free from external stresses in the expanded state, and wherein an operating state exists, which the rotor assumes while operating under load, wherein the reinforcement elements in the rotor in the operating state run in a stretched manner, at least sectionally.

2. The rotor of claim 1, wherein the reinforcement elements in the operating state of the rotor run in a stretched manner at least in part in regions of the rotor in which this experiences an elongation stress and run substantially in the direction of the elongation stress.

3. The rotor of claim 1, wherein more than half of the reinforcement elements are arranged in regions of the rotor experiencing elongation stresses in the operating state.

4. The rotor of claim 1, wherein there are substantially no differences between the expanded state and the operating state in respect of outer form.

5. The rotor of claim 1, wherein reinforcement elements are provided, which extend beyond the axis of rotation in a radial direction.

6. The rotor of claim 1, wherein, in the operating state, at least some of the reinforcement elements, run sectionally straight.

7. The rotor of claim 1, wherein, in the operating state, at least some of the reinforcement elements, run along a longitudinal direction of the one or more impeller elements with a smaller curvature than neutral fibers of the one or more impeller elements.

8. The rotor of claim 1, wherein the plastic material of the rotor has a Shore hardness <100 D.

9. The rotor of claim 1, wherein a first proportion of more than 30% of the reinforcement elements in the expanded state of the rotor runs substantially stretched from a portion disposed closest to the axis of rotation to a second portion disposed further from the axis of rotation.

10. The rotor of claim 9, wherein the first proportion of the reinforcement elements runs substantially perpendicularly to the axis of rotation.

11. The rotor of claim 1, wherein a first proportion of the reinforcement elements, the first proportion being more than 30% of the reinforcement elements, has a length corresponding to at least 30% of a maximum height of the one or more impeller elements, measured in a radial direction of the rotor in the expanded state.

12. The rotor of-claim 1, wherein a diameter of the reinforcement elements is less than 40 micrometers.

13. The rotor of claim 1, wherein a surface of the reinforcement elements having an adhesion promoter.

14. The rotor of claim 1, wherein a proportion of reinforcement elements in the expanded state of the rotor runs transversely to the reinforcement elements of a first proportion.

15. The rotor of claim 1, wherein the reinforcement elements are at least in part fabric portions with fibers running longitudinally and transversely.

16. The rotor of claim 1, wherein the reinforcement elements are film strips, wherein a length of the film strips is at least three times greater than a width of the film strips.

17. The rotor of claim 1, wherein the reinforcement elements are surrounded by the plastic material from which the rotor is predominantly made, at least to a proportion of 90%.

18. The rotor of claim 1, wherein the plastic material in which the reinforcement elements are embedded has different properties, at least in regions, on a side of the one or more impeller elements not loaded by a fluid counter-pressure during operation compared to a side of the one or more impeller elements that is loaded by the fluid counter-pressure.

19. The rotor of claim 1, wherein the reinforcement elements in the expanded state of the rotor, without a fluid counter-pressure, are present in a form stretched to such an extent that when transitioning to a third state, which constitutes the operating state with the fluid counter-pressure, the reinforcement elements are lengthened by less than 5% wherein lengthening is measured as a distance between two ends of a reinforcement element.

20. The rotor of claim 1, wherein in the expanded state of the rotor with a fluid counter-pressure at least a portion of the reinforcement elements run in a stretched and straight manner in at least one region of an impeller element of the one or more impeller elements, wherein said impeller element is curved.

21. The rotor of claim 20, wherein in a curved region of an impeller element of the one or more impeller elements, at least two portions of reinforcement elements run in a stretched and straight manner, wherein directions in which the reinforcement elements of the portions run are parallel within the same portion, but are different between the two different portions.

22. The rotor of claim 1, wherein a length of at least 30% of the reinforcement elements is greater than an average thickness of the one or more impeller elements.

23. The rotor of claim 1, wherein the reinforcement elements are introduced into the plastic material in which said reinforcement elements are embedded in an injection molding method and, wherein the reinforcement elements have a partially curved course along a flow of the plastic material into the injection mold during a time for which the rotor is disposed in an injection mold.

24. The rotor of claim 1, wherein in the operating state, with a fluid counter-pressure, at least a portion of the reinforcement elements runs in a stretched and straight manner in at least one region of an impeller element of the one or more impeller elements, wherein said impeller element is curved.

25. The rotor of claim 1, wherein the plastic material in which the reinforcement elements are embedded has different properties, at least in regions, on a side of the one or more impeller elements not loaded by a fluid counter-pressure during operation compared to a side of the one or more impeller elements that is loaded by the fluid counter-pressure, wherein the plastic material is more heavily cross-linked on the side not loaded by the fluid counter-pressure.

26. The rotor of claim 1, wherein the plastic material in which the reinforcement elements are embedded has different properties, at least in regions, on a side of the one or more impeller elements not loaded by a fluid counter-pressure during operation compared to a side of the one or more impeller elements that is loaded by the fluid counter-pressure, wherein the plastic material is more heavily shrunk on the side not loaded by the fluid counter-pressure, and wherein the side not loaded by the fluid counter-pressure comprises a support shrunk on the one or more impeller elements, said support being provided in the form of one or more fibers.

27. A rotor for a compressible fluid pump configured to be expanded and compressed radially between a first, compressed state and a second, expanded state, that the rotor comprising at least one element which is produced by injection molding with simultaneous addition of reinforcement elements in the expanded state, wherein the reinforcement elements are surrounded on all sides by an injection molding material and are present in a stretched form at least in part in the second, expanded state.

28. A method for producing the rotor of claim 1 by means of a molding method in which the material of the one or more impeller elements is introduced into volumes of the one or more impeller elements in a radial direction with respect to the axis of rotation, in such a way that a molding material flows into the volume of each individual impeller element of the one or more impeller elements in the radial direction.

29. The method of claim 28, wherein the rotor, after the molding, is subjected to a treatment which causes a different shrinkage of the molding material on an opposite side of the one or more impeller elements loaded by a fluid counter-pressure during operation than on an opposite side.

30. The method of claim 28, wherein a shrinkable layer is applied to at least one of the one or more impeller elements on the side opposite the side of the one or more impeller elements exposed to a fluid counter-pressure during operation.

31. The method of claim 28, wherein the rotor is formed by a mold, wherein the mold comprises overflow channels in the volumes of the one or more impeller elements at radial edges thereof, wherein the overflow channels are configured to enable an uninterrupted flow of the molding material in a radial direction.

32. The method of claim 28, wherein the rotor is formed by a, the mold characterized by at least two different injection openings.

33. The method of claim 28, wherein the rotor, after the molding, is subjected to a treatment which causes a different cross-linking of the molding material on a side of the one or more impeller elements loaded by a fluid counter-pressure during operation than on an opposite side.

34. A method for producing the rotor of claim 1, wherein the rotor is produced by molding wherein the molding is carried out in two successive phases with different injection directions.

35. A method for producing the rotor of claim 1, wherein the rotor is produced by molding, wherein the molding is carried out in two successive phases from two different injection points.

* * * * *

UNITED STATES PATENT AND TRADEMARK OFFICE
CERTIFICATE OF CORRECTION

PATENT NO. : 10,801,511 B2
APPLICATION NO. : 15/570128
DATED : October 13, 2020
INVENTOR(S) : Thorsten Siess and Mario Scheckel It is certified that error appears in the above-identified patent and that said Letters Patent is hereby corrected as shown below:

In the Specification

Column 8, Line 60:
Now reads: "material"; should read -- material. --

In the Claims

Column 19, Claim 12, Line 7:
Now reads: "of-claim"; should read -- of claim --

Signed and Sealed this
Fifteenth Day of February, 2022

Drew Hirshfeld
*Performing the Functions and Duties of the
Under Secretary of Commerce for Intellectual Property and
Director of the United States Patent and Trademark Office*